(12) United States Patent
Carnes et al.

(10) Patent No.: US 9,215,516 B2
(45) Date of Patent: Dec. 15, 2015

(54) SYSTEM AND METHOD FOR IDENTIFYING NEWLY CAPTURED CONFIGURATION PARAMETERS OF A PLURALITY OF MEDICAL DEVICES

(71) Applicant: Covidien LP, Mansfield, MA (US)

(72) Inventors: Tony C. Carnes, Gainesville, FL (US); William A. Jordan, II, Westminster, CO (US)

(73) Assignee: COVIDIEN LP, Mansfield, MA (US)

( * ) Notice: Subject to any disclaimer, the term of this patent is extended or adjusted under 35 U.S.C. 154(b) by 314 days.

(21) Appl. No.: 13/835,095

(22) Filed: Mar. 15, 2013

(65) Prior Publication Data

US 2014/0266783 A1 Sep. 18, 2014

(51) Int. Cl.
| | |
|---|---|
| *G08C 15/06* | (2006.01) |
| *H04Q 9/02* | (2006.01) |
| *G01F 15/06* | (2006.01) |
| *A61B 5/00* | (2006.01) |
| *G06F 19/00* | (2011.01) |
| *A61B 5/0205* | (2006.01) |

(52) U.S. Cl.
CPC *H04Q 9/02* (2013.01); *A61B 5/002* (2013.01); *G01F 15/063* (2013.01); *G06F 19/3412* (2013.01); *A61B 5/02055* (2013.01)

(58) Field of Classification Search
CPC ........ G01F 15/063; H04Q 9/02; A61B 5/002; A61B 5/02055; G06F 19/3412
USPC ......... 340/870.03, 531, 539.12; 600/300–302
See application file for complete search history.

(56) References Cited

U.S. PATENT DOCUMENTS

| | | | | |
|---|---|---|---|---|
| 6,057,758 | A * | 5/2000 | Dempsey et al. | 340/539.12 |
| 6,871,211 | B2 * | 3/2005 | Labounty et al. | 709/203 |
| 7,062,251 | B2 * | 6/2006 | Birkett et al. | 455/400 |
| 8,051,414 | B2 | 11/2011 | Stender et al. | |
| 8,352,038 | B2 | 1/2013 | Mao et al. | |
| 8,838,136 | B2 * | 9/2014 | Carnes et al. | 455/456.1 |
| 2005/0283198 | A1 | 12/2005 | Haubrich et al. | |
| 2007/0100397 | A1 | 5/2007 | Seeberger et al. | |
| 2010/0234718 | A1 * | 9/2010 | Sampath et al. | 600/407 |
| 2011/0289497 | A1 * | 11/2011 | Kiaie et al. | 717/171 |
| 2012/0016305 | A1 * | 1/2012 | Jollota et al. | 604/151 |
| 2012/0029304 | A1 * | 2/2012 | Medina et al. | 600/300 |
| 2012/0096451 | A1 | 4/2012 | Tenbarge et al. | |
| 2012/0232918 | A1 | 9/2012 | Mack et al. | |
| 2013/0086162 | A1 * | 4/2013 | Smith | 709/204 |
| 2013/0104120 | A1 * | 4/2013 | Arrizza et al. | 717/173 |
| 2013/0132465 | A1 | 5/2013 | Brown | |

* cited by examiner

*Primary Examiner* — Eric M Blount
(74) *Attorney, Agent, or Firm* — Carter, DeLuca, Farrell & Schmidt, LLP

(57) ABSTRACT

A medical device communication system is presented including a plurality of medical devices, a data collection module for receiving at least pre-defined configuration parameters from each of the plurality of medical devices, and a medical device driver communicating with the data collection module, the medical device driver automatically capturing post-defined configuration parameters from the plurality of medical devices. The medical device communication system includes at least one remote device configured to receive the pre-defined and post-defined configuration parameters from the data collection module. The post-defined configuration parameters are received after the medical device driver is initially written and after initial electrical communication is established between the medical device driver and the data collection module. The medical device driver is prevented from being re-written each time post-defined configuration parameters are transmitted from at least one of the plurality of medical devices to the data collection module.

20 Claims, 10 Drawing Sheets

SYSTEM AND METHOD FOR IDENTIFYING NEWLY CAPTURED CONFIGURATION PARAMETERS OF A PLURALITY OF MEDICAL DEVICES

TECHNICAL FIELD

The present disclosure relates to medical devices and, more particularly, to systems and methods for medical devices that display patient-related data.

BACKGROUND

A wide variety of devices have been developed for non-invasively monitoring physiologic characteristics of patients. For example, an oximetry sensor system may non-invasively detect various patient blood flow characteristics, such as blood-oxygen saturation of hemoglobin in blood, volume of individual blood pulsations supplied to tissue, and/or the rate of blood pulsations corresponding to each heart beat of a patient. During operation, the oximeter sensor emits light and photo-electrically senses the absorption and/or scattering of the light after passage through perfused tissue. A photo-plethysmographic waveform, which corresponds to cyclic attenuation of optical energy through the patient's tissue, may be generated from the detected light. Additionally, one or more physiologic characteristics may be calculated based upon an amount of light absorbed or scattered. More specifically, the light passed through tissue may be selected to be of one or more wavelengths that may be absorbed and/or scattered by the blood in an amount correlative to the amount of the blood constituent present in the blood. The amount of light absorbed and/or scattered may then be used to estimate the amount of blood constituent in tissue using various algorithms.

Many medical devices support multiple output techniques. For example, certain medical devices may output data in a textual format while other medical devices may output data in binary format. Certain medical devices may have different rates of output for the output data.

The automated capture of sensed physiologic values or output data from one or multiple medical devices may lead to improved patient care. However, the act of capturing and displaying the data/information from medical sensors does not necessarily improve care. What may improve care is the ability to present the captured data/information in new ways and to identify cause and effect relationships for such captured data/information.

SUMMARY

The present disclosure relates to systems and methods that generally include a plurality of medical devices, a data collection module for receiving at least pre-defined configuration parameters from each of the plurality of medical devices, and a medical device driver electrically communicating with the data collection module, the medical device driver automatically capturing post-defined configuration parameters from at least one of the plurality of medical devices. The systems and methods also include at least one remote device configured to receive the pre-defined and post-defined configuration parameters from the data collection module. The post-defined configuration parameters are received after the medical device driver is initially written and after initial electrical communication is established between the medical device driver and the data collection module.

The aspects and features of the present disclosure are advantageous in that they provide pre-defined and post-defined configuration parameters, such as a frequency parameter, a selection parameter, a compression parameter, an output parameter, and a port parameter. The aspects and features of the present disclosure are advantageous in that they provide at least one remote device that includes an oximetry monitor configured to display the pre-defined and post-defined configuration parameters. The aspects and features of the present disclosure are advantageous in that they also provide the post-defined configuration parameters with identification information, including one or mode codes or offsets to facilitate parsing of the post-defined configuration parameters by the medical device driver. The identification information further includes one or more labels associated with the post-defined configuration parameters and at least one of a length, a data type, and an abbreviation of the post-defined configuration parameters. The aspects and features of the present disclosure are advantageous in that they allow the medical device driver to be prevented from being re-written each time post-defined configuration parameters are transmitted from at least one of the plurality of medical devices to the data collection module.

Certain embodiments of the present disclosure may include some, all, or none of the above advantages and/or one or more other advantages readily apparent to those skilled in the art from the drawings, descriptions, and claims included herein. Moreover, while specific advantages have been enumerated above, the various embodiments of the present disclosure may include all, some, or none of the enumerated advantages and/or other advantages not specifically enumerated above.

BRIEF DESCRIPTION OF THE DRAWINGS

The present disclosure and its various aspects and features are described hereinbelow with reference to the accompanying drawings, wherein.

Figure 1:
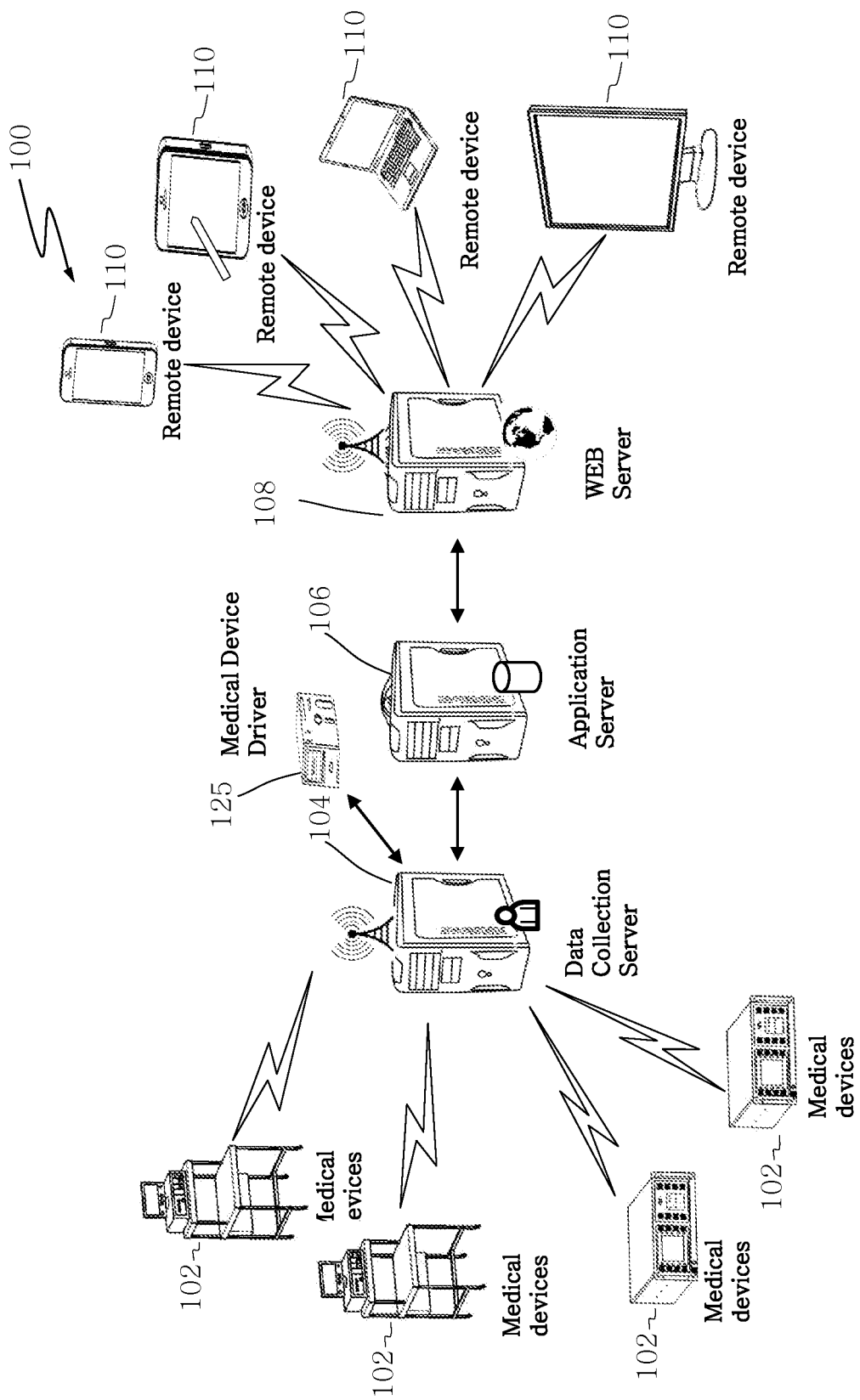
FIG. 1 is a perspective view of an illustrative embodiment of a medical communication system, in accordance with an aspect of the present disclosure.

The figures depict embodiments of the present disclosure for purposes of illustration only. One skilled in the art will readily recognize from the following disclosure that alternative embodiments of the structures and methods illustrated herein may be employed without departing from the principles of the present disclosure described herein.

DETAILED DESCRIPTION

Although the present disclosure will be described in terms of specific embodiments, it will be readily apparent to those skilled in this art that various modifications, rearrangements and substitutions may be made without departing from the spirit of the present disclosure. The scope of the present disclosure is defined by the claims appended hereto.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

The term "clinician" refers to any medical professional (i.e., doctor, surgeon, nurse, or the like) performing and/or monitoring and/or supervising a medical procedure involving the use of exemplary embodiments described herein.

Within this disclosure, the term "user" may also include, in addition to human users: computers, automated systems, controllers, robotic devices, and other electro-mechanical devices, systems, configurations/apparatuses using software (or code).

The term "application" in the disclosed embodiments refers to at least a program designed for end users of a computing device, such as a word processing program, a database program, a browser program, a spreadsheet program, a gaming program, and the like. An application is distinct from systems programs, which consist of low-level programs that interact with the computing device at a very basic level, such as an operating system program, a compiler program, a debugger program, programs for managing computer resources, and the like.

The term "module" may refer to a self-contained component (unit or item) that is used in combination with other components and/or a separate and distinct unit of hardware or software that may be used as a component in a system, such as a wireless or non-wireless communication system. The term "module" may also refer to a self-contained assembly of electronic components and circuitry, such as a stage in a computer that is installed as a unit.

The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

Conventional medical devices output a fixed format of data to external systems. However, the amount of relevant output data desired by one external system may be far different from another external system. In addition, the transmission of potentially extraneous or redundant output data may lead to network congestion. In certain embodiments of the present disclosure, a configuration interface is provided that allows end-users to customize patient parameters and other data that is transmitted from a patient parameter receiving device such as a data collection server described in more detail below. Thus, at least one advantage of the exemplary embodiments of the present disclosure includes a reduction in network traffic and parsing overhead at a receiving system by selecting a subset of patient parameters and other data to be transmitted.

Another advantage of the exemplary embodiments of the present disclosure includes a capacity to extend a single serial port to multiple ports with different protocols per port to allow different systems to communicate with a medical device in different ways. In certain embodiments of the present disclosure, a user may implement the configuration interface to specify: (1) a selection parameter that indicates the desired patient parameters to be parsed and passed on by the configuration interface; (2) a frequency parameter that indicates the frequency at which the data should be captured and passed (e.g., switching between any of a number of baud rates such as 2400, 4800, 9600, 14400, 28800, and 57600 baud rates or the frequency parameter may be throttled up or down to transmit patient parameters (or a subset of patient parameters) depending on system needs); (3) a compression parameter that indicates certain outputs from a medical device to be captured, compressed, and transmitted together to a receiving system at a specified interval; (4) an output parameter that indicates a selection of one of several protocols for transmitting the data to a receiving system; and (5) a port parameter that indicates which forwarding port is associated with which output protocol.

Patient data may include any patient identifiers, medical history, clinician notes, alarm thresholds, alarm events, device settings, measurements of values indicating physiologic conditions, such as oxygen saturation levels, pulse rates, heart rates, other vital signs, and any other data input to or output from medical devices. It is noted that monitored and/or measured physiologic parameters include at least one of: oxygen saturation, pulse rate, respiration rate, heart rate, temperature, arterial pressure, blood pressure, and hydration status. However, one skilled in the art may monitor any known physiologic parameters. Medical devices may be any devices that are used for monitoring, tracking and/or treating patients. For example, medical devices may include a ventilator connected to a patient to deliver respiration therapy, a pulse oximeter that monitors the oxygen saturation of a patient's blood, a device for tracking a patient within a hospital with or without monitoring a physiologic condition, as well as other medical devices known to those of skill in the art. Medical devices may include a component for identifying the particular medical device, including, but not limited to, radio frequency identification chips and unique bar codes.

The techniques of the present disclosure may be used in conjunction with any type of displayed medical data/information. For example, the medical data/information may be collected using a particular sensor or set of sensors, such as regional oxygen saturation sensors. By way of example, an INVOS® cerebral/somatic sensor, such as an OxyAlert™ NIR sensor by Somanetics or a SomaSensor® sensor by Somanetics, which may include one or more emitters and a pair of detectors for determining site-specific oxygen levels, may represent such sensors. In addition, when analyzing data via the INVOS® cerebral/somatic sensor, the present techniques allow a medical professional or user to highlight the area under the curve or plot for each channel of the INVOS® sensor. The present techniques may also be used in conjunction with other types of medical sensors, such as pulse oximetry sensors or carbon dioxide sensors. One skilled in the art may contemplate using a plurality of different sensors for measuring and/or monitoring a plurality of different physiologic parameters.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

FIG. 1 illustrates an example system 100 for establishing communication with medical devices, according to exemplary embodiments of the present disclosure. System 100 includes one or more medical devices 102, a data collection server 104, an application server 106, a web server 108, one or more remote devices 110, and a medical device driver 125. According to one embodiment, system 100 is configured to monitor medical devices 102 and configured to transform patient parameters into display parameters. In certain embodiments, medical devices 102 generate patient parameters or store patient parameters input by a user, such as a clinician or medical professional. Each medical device 102 may be connected to a data collection server 104, which stores the patient parameters in a database. Application server 106 retrieves the patient parameters from the database and processes the patient parameters into display parameters for web server 108. Remote devices 110 request and receive the display parameters and display the display parameters through a browser, thereby enabling clinicians using the remote devices 110 to view the display parameters in remote locations. As described in more detail below, a configuration interface at data collection server 104 includes logic that may receive, parse, interpret, and translate patient parameters received from different medical devices 102.

Although this particular implementation of system 100 is illustrated and primarily described, the present disclosure contemplates any suitable implementation of system 100 according to particular needs. For example, although this implementation of the configuration interface is illustrated with remote devices 110 that may be using a web interface or a client/server interface, the exemplary embodiments of the disclosure contemplate any suitable implementation of the configuration interface. In addition, a component of system 100 may include any suitable arrangement of elements, for example, an interface, logic, memory, other suitable element, or a combination of any of the preceding. An interface receives input, sends output, processes the input and/or output, performs other suitable operation, or performs a combination of any of the preceding. An interface may comprise hardware and/or software.

System 100 may include one or more medical devices 102. Medical devices 102 may be any devices that are used for tracking or treating patients. For example, medical devices 102 may include a ventilator connected to a patient to deliver respiratory therapy. As another example, medical devices 102 may include a pulse oximeter that monitors the oxygen saturation of a patient's blood. As another example, medical devices 102 may include a device for tracking a patient without monitoring physiological conditions. In short, medical devices 102 may include any suitable combination of software, firmware, and hardware used to support any medical function and/or operation. It should be noted that any suitable number of medical devices 102 may be included in system 100. In addition, there may be multiple groups of medical devices 102 in the system 100.

According to one embodiment, in addition to performing a medical function and/or operation, medical devices 102 may generate output data tracked by medical devices 102. For example, the ventilator may generate entries indicating the average volume of air expelled in each breath. The ventilator may generate entries including the parameter settings used by the ventilator and an identification of whether any alarms have been triggered. The ventilator may store the generated entries in local memory and output the entries. In some embodiments, medical devices 102 may generate output data that is related to tracking patient identifications or locations, without necessarily generating data related to a physiological condition. In certain embodiments, medical devices 102 may output data in response to a data request. In certain other embodiments, medical devices 102 may constantly stream output data.

Medical devices 102 may be communicatively coupled to data collection server 104 via a network, according to one embodiment. The network facilitates wired or wireless communication. The network may communicate, for example, IP packets, Frame Relay frames, Asynchronous Transfer Mode (ATM) cells, voice, video, data, and other suitable information between network addresses. The network may include one or more local area networks (LANs), radio access networks (RANs), metropolitan area networks (MANs), wide area networks (WANs), all or a portion of the global computer network known as the Internet, and/or any other communication system or systems at one or more locations. In certain embodiments, medical devices may be communicatively coupled to other suitable devices including data collection server 104, application server 106, web server 108, remote devices 110, and medical device driver 125.

System 100 may include one or more data collection servers 104, referred to primarily in the singular throughout this disclosure. Data collection server 104 may include one or more electronic computing devices operable to receive, transmit, process, and store data associated with system 100. For example, data collection server 104 may include one or more general-purpose PCs, MACINTOSH® computers, workstations, UNIX® system based computers, server computers, one or more server pools, or any other suitable devices. In certain embodiments, data collection server 104 includes a web server. In short, data collection server 104 may include any suitable combination of software, firmware, and hardware. Although a single data collection server 104 is illustrated, the present disclosure contemplates system 100 including any suitable number of data collection servers 104. Moreover, although referred to as a data collection server, the present disclosure contemplates data collection server 104 comprising any suitable type of processing device or devices.

According to one embodiment, data collection server 104 receives patient parameters from medical devices 102. For example, data collection server 104 may request patient parameters from a medical device 102 and receives patient parameter sets from the medical device 102 in response to the request. As another example, data collection server 104 may receive streamed output data from a medical device 102. As another example, data collection server 104 may be configured to periodically request new data from medical device 102. Data collection server 104 may map the received patient parameters to match internal fields in the database and then transmit the data to a database, according to one embodiment. The stored data may be accessed by application server 106.

System 100 may include one or more application servers 106, referred to primarily in the singular throughout this disclosure. Application server 106 may include one or more electronic computing devices operable to receive, transmit, process, and store data associated with system 100. For example, application server 106 may include one or more general-purpose PCs, workstations, UNIX® system based computers, server computers, one or more server pools, or any other suitable devices. In short, application server 106 may include any suitable combination of software, firmware, and hardware. Although a single application server 106 is illustrated, the present disclosure contemplates system 100 including any suitable number of application servers 106. Moreover, although referred to as an application server, the present disclosure contemplates application server 106 comprising any suitable type of processing device or devices.

According to one embodiment, application server 106 creates a data service, which runs on a conventional web services platform for transmitting data to web server 108. For example, application server 106 may create webpage data using the patient parameters, and that webpage data is transmitted to web server 108 for display. Application server 106 may maintain an activity log that logs data requests from remote devices 110 to track certain activities performed at the remote devices 110. Therefore, if a clinician selects a particular patient representation to zoom in and view ventilator data specific to that patient, that selection may trigger a data request that is logged by application server 106. When creating the webpage data, application server 106 may compare the current parameter settings of the ventilator, as indicated by entries in the patient parameter set, to prior parameter settings. If any changes are detected, application server 106 may flag those changes for presentation to users on remote devices 110. Specifically, application server 106 may create data causing the depiction of the changed patient parameters on the remote devices 110 to change color. Application server 106 may create additional data that causes a pop-up window to appear on the mobile device when any of the changed patient parameters are selected. That window may list all of the changed patient parameters and provides a single button through which a user may indicate that that the changed patient parameters have been viewed. If that button is activated, the mobile device may transmit a message to application server 106 and application server 106 may then unflag those patient parameters, such that the depiction of those patient parameters on remote device 110 may return to the original color. In certain embodiments, application server 106 may transmit data directly to remote devices 110.

System 100 may include one or more web servers 108, referred to primarily in the singular throughout this disclosure. Web server 108 may include one or more electronic computing devices operable to receive, transmit, process, and store data associated with system 100. For example, web server 108 may include one or more general-purpose PCs, MACINTOSH® computers, workstations, UNIX® system based computers, server computers, one or more server pools, or any other suitable devices. In short, web server 108 may include any suitable combination of software, firmware, and hardware. Although a single web server 108 is illustrated, the present disclosure contemplates system 100 including any suitable number of web servers 108. Moreover, although referred to as a web server, the present disclosure contemplates web server 108 comprising any suitable type of processing device or devices.

According to one embodiment, web server 108 creates a data service that runs on a conventional web services platform for receiving data from application server 106 and transmitting data to remote devices 110. For example, web server 108 may receive webpage data from application server 106 and transmitted, upon request in certain embodiments, to remote devices 110.

System 100 may include one or more remote devices 110. Remote devices 110 may be any device that provides output to and may receive input from a user, such as a clinician. Each remote device 110 may include one or more computer systems at one or more locations. Each computer system may include any appropriate input devices (such as a keypad, touch screen, mouse, or other device that may accept input), output devices, mass storage media, or other suitable components for receiving, processing, storing, and communicating data. Both the input device and output device may include fixed or removable storage media such as a magnetic computer disk, CDROM, or other suitable media to both receive input from and provide output to a user. Each computer system may include a personal computer, workstation, network computer, kiosk, wireless data port, personal data assistant (PDA), one or more processors within these or other devices, or any other suitable processing device.

According to one embodiment, remote devices 110 display one or more web pages hosted by application server 106 and/or web server 108 with patient parameters from medical devices 102. For example, a clinician may activate a browser on remote device 110 and navigate to the web page hosted by web server 108. The browser may render the web page, which includes patient parameters generated by medical devices 102. The web page may provide a summary of all the medical devices 102 under a clinician's responsibility. In addition, the web page may display a detailed view that displays at least specific device data, therapy parameter data, and alarm status data.

Although FIG. 1 depicts separate devices for data collection server 104, application server 106, and web server 108, it will be readily apparent that the functions of these devices may be combined into a single device that receives patient parameters from medical devices 102 and transforms the patient parameters into display parameters. It will also be understood that this single device may alternatively transmit the display parameters to remote device 110. In certain embodiments, data collection server 104 may be a bedside device that receives patient parameters from medical devices 102.

It will also be understood that the functions may be allocated differently than shown, with application server 106 additionally performing the functions of the web server 108 or the functions of data collection server 104. In another embodiment, a single device may receive patient parameters, transform those patient parameters into display parameters, and display the display parameters on a screen.

A user of system 100 may connect many different types of medical devices 102 to examine a combination of patient parameters. Each medical device 102 may output a fixed format of data to data collection server 104. In certain embodiments, there may be a certain amount and type of relevant output data from a particular medical device for some systems and a different amount and type of relevant output data from for other systems. In addition, there may be additional issues with communicating large amounts of information from medical devices 102 to multiple data collection servers 104 across a network including network bandwidth issues and end-system consumption issues.

In certain embodiments of the disclosure, system 100 may include a configuration interface to address these concerns. The configuration interface may refer to any suitable hardware and/or software operable to be configured to filter patient parameters received from different medical devices 102 at data collection server 104. Filtering patient parameters may refer to specifying a certain subset of patient parameters to be transmitted by data collection server 104 based on configuration parameters such as a selection parameter that indicates the desired patient parameters to be parsed and passed on by the configuration interface, a frequency parameter that indicates the frequency at which the data should be captured and passed (e.g., switching from a 9600 baud rate to a 14400 baud rate; baud rate or transmitting data at selected intervals, e.g., 10 seconds), a compression parameter that indicates certain outputs from a medical device to be captured, compressed, and transmitted together in a subset at a specified interval, an output parameter that indicates a selection of one of several output protocols for transmitting the data to a receiving system, and a port parameter that indicates which forwarding port is associated with which output protocol. Therefore, the configuration interface may reduce network traffic, reduce parsing overhead, and ensure that desired information is transmitted. Additional details of exemplary embodiments of the configuration interface are described in greater detail below with reference to FIGS. 2-4.

Figure 2:
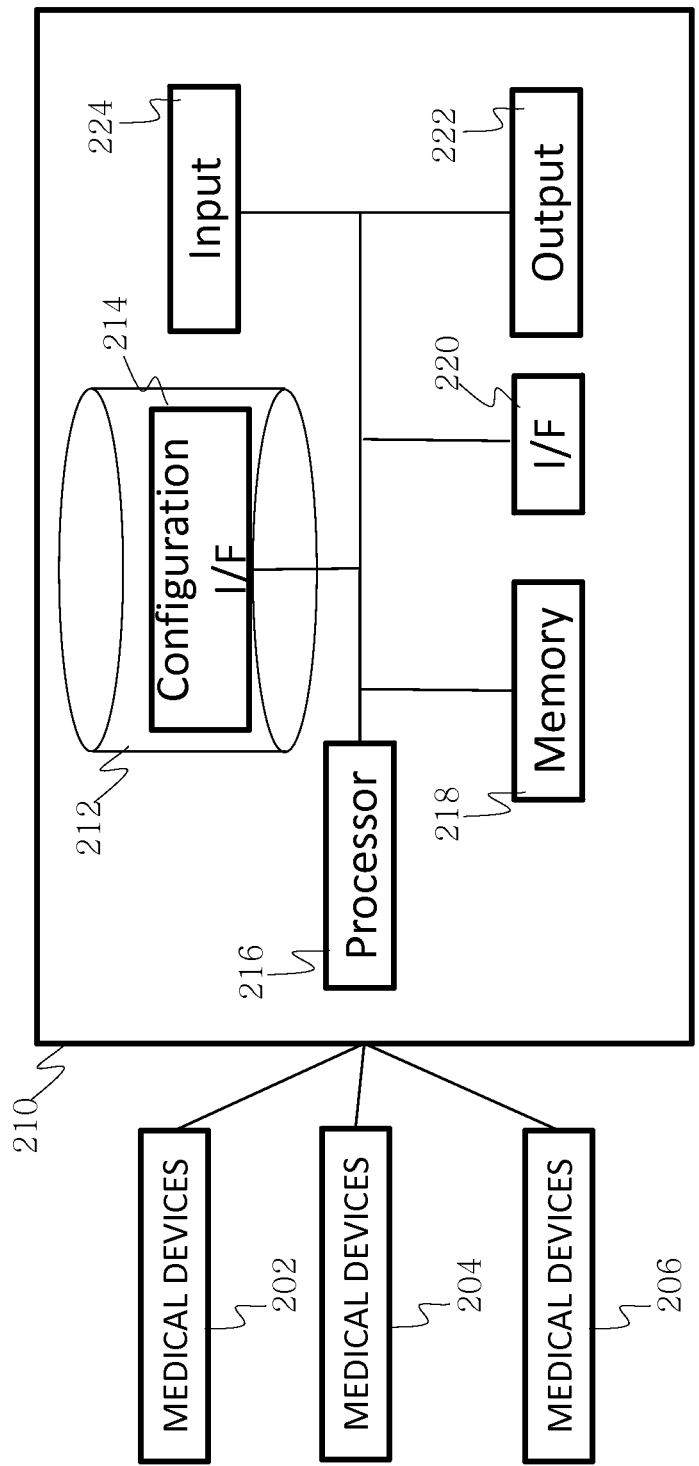
FIG. 2 is an exemplary block diagram of the data collection server of FIG. 1, in accordance with an aspect of the present disclosure.

FIG. 2 illustrates an example data collection server 210 of the system 100 for establishing communication with medical devices in FIG. 1, according to certain embodiments of the present disclosure. Data collection server 210 may be substantially similar to data collection server 104 of FIG. 1. In FIG. 2, a data collection server 210 is shown as a server communicatively coupled with medical devices 202, 204, and 206, which devices may be substantially similar to medical devices 102 of FIG. 1. Data collection server 210 includes a storage device 212, a configuration interface 214, a processor 216, a memory 218, a communication interface (IF) 220, an output device 222, and an input device 224, which are described in further detail below. Although this particular implementation of data collection server 210 is illustrated and primarily described, the present disclosure contemplates any suitable implementation of data collection server 210 according to particular needs.

Storage device 212 may include any suitable device operable for storing data and instructions. Storage device 212 may include, for example, a magnetic disk, flash memory, optical disk, or other suitable data storage device.

Configuration interface 214 may include any suitable logic embodied in computer-readable media, and when executed, that is operable to be configured to filter patient parameters received from different medical devices 202-206. For example, configuration interface 214 may include logic for receiving a first input indicative of first configuration parameters for a first medical device from a user and a second input indicative of second configuration parameters for a second medical device from the user. The first configuration parameters may include at least one of a frequency parameter, a selection parameter, a compression parameter, an output parameter, and a port parameter. The configuration interface 214 may receive first patient parameters from the first medical device and second patient parameters from the second medical device. The configuration interface 214 may transmit a first selected subset of the first patient parameters based on the first configuration parameters and transmit a second selected subset of the second patient parameters based on the second configuration parameters. Additional details of configuration interface 214 and configuration parameters are provided below with reference to FIG. 3.

Processor 216 may include any suitable device operable to execute instructions and manipulate data to perform operations for configuration interface 214, for example, any type of central processing unit (CPU). Memory 218 may include any computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server). Memory 218 may comprise any other computer-readable tangible medium, or a combination of any of the preceding.

I/F 220 may include any suitable device operable to receive input for configuration interface 214, send output from configuration interface 214, perform suitable processing of the input or output or both, communicate to other devices, or any combination of the preceding. I/F 220 may include appropriate hardware (for example, a modem, network interface card, etc.) and software, including protocol conversion and data processing capabilities, to communicate through a LAN, WAN, or other communication system that allows configuration interface 214 to communicate to other devices. I/F 220 may include one or more ports, conversion software, or a combination of any of the preceding.

Output device 222 may include any suitable device operable for displaying information to a user, for example, a video display, a printer, a plotter, or other suitable output device. In certain embodiments, output device 222 may reformat data in any suitable format to be transmitted to other systems.

Input device 224 may include any suitable device operable to input, select, and/or manipulate various data and information, for example, a keyboard, mouse, graphics tablet, joystick, light pen, microphone, scanner, or other suitable input device.

Modifications, additions, or omissions may be made to data collection server 210 without departing from the scope of the present disclosure. The components of data collection server 210 may be integrated or separated. Moreover, the operations of data collection server 210 may be performed by more, fewer, or other components. For example, although configuration interface 214 is displayed as part of storage device 212, configuration interface 214 may be stored in any suitable location, including in another suitable device shown in FIG. 1, and the operations of configuration interface 214 may be performed by more than one component. Additionally, operations of data collection server 210 may be performed using any suitable logic. As used in this document, "each" refers to each member of a set or each member of a subset of a set. Further details of an example data collection server 210 and the operations of configuration interface 214 are provided below with reference to FIG. 3.

Figure 3:
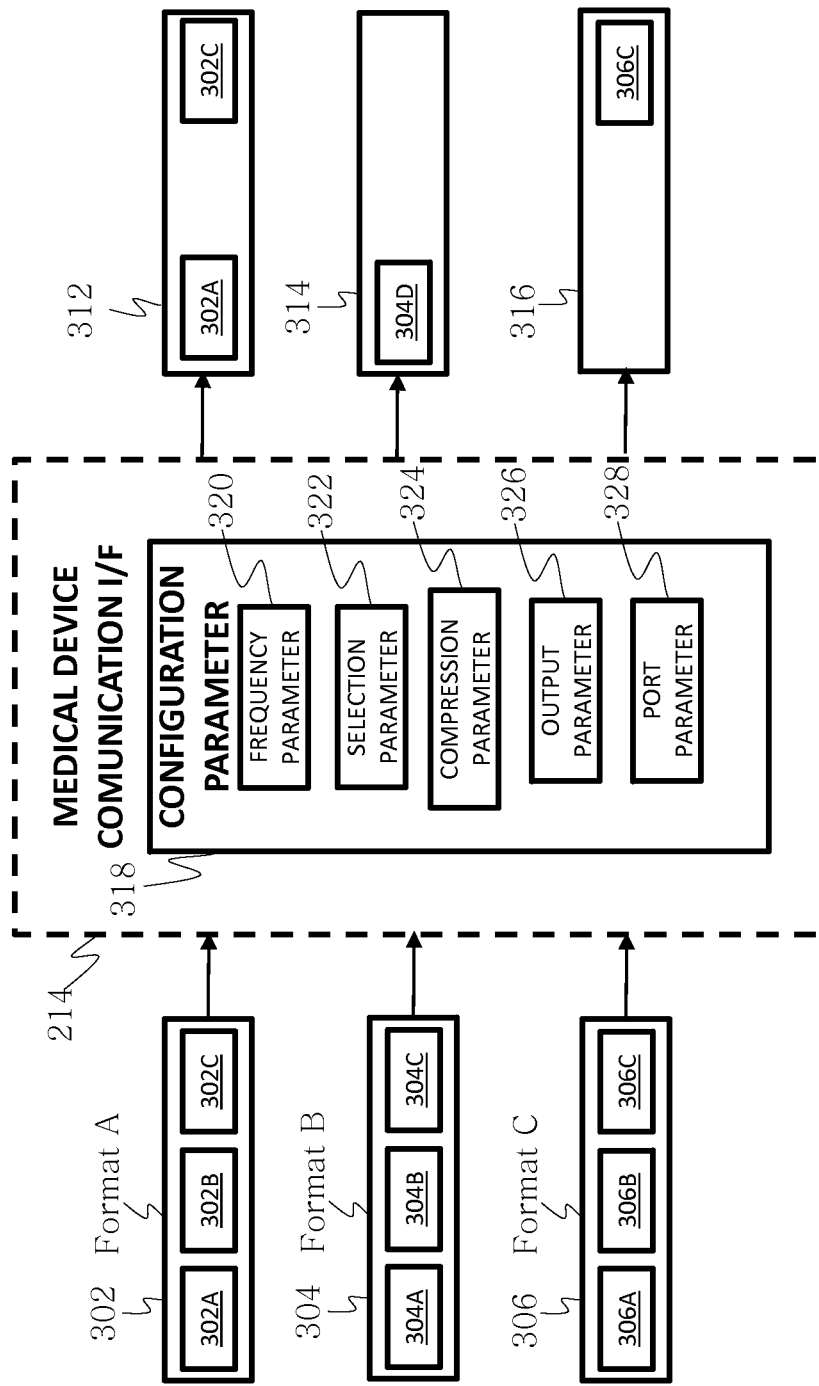
FIG. 3 is an exemplary block diagram of an operation of a configuration interface, in accordance with an aspect of the present disclosure.

FIG. 3 illustrates one embodiment of an example operation of configuration interface 214 of FIG. 2, according to certain embodiments of the present disclosure. The illustrated embodiment includes a format 302, a format 304, and a format 306 and associated patient parameters, such as patient parameters 302A, 302B, and 302C in format 302, which may be generated by respective medical devices, such as medical devices 102 in FIG. 1. A format may refer to any systematic arrangement of patient parameters and may include any of a data speed, data type, data count, data encoding, data syntax, data format, or any combination thereof. In certain embodiments, each of formats 302-306 may represent a particular proprietary format for medical devices 102. For example, format 302 may be associated with patient parameters output from a first medical device 102 in FIG. 1 and format 304 may be associated with a second medical device 102 in FIG. 1.

According to certain embodiments of the disclosure, formats 302, 304, and 306 as well as their associated patient parameters may be filtered at configuration interface 214 to specify, for example: certain desired parameters to be parsed and transmitted, a frequency at which the data should be captured and transmitted, a compression factor to allow for multiple outputs from the medical device to be captured, compressed, and transmitted together at a specified interval, a selection of one of several output protocols for transmission, and a forwarding port associated with a certain output protocol. These configuration parameters 318 may be a frequency parameter 320, a selection parameter 322, a compression parameter 324, an output parameter 326, and a port parameter 328.

For example, in the illustrated embodiment, patient parameters 302A, 302B, and 302C of format 302 may be filtered to identify a subset of patient parameters to be parsed and transmitted, such as patient parameters 302A and 302C in format 312. As another example, in the illustrated embodiment, patient parameters 304A, 304B, and 304C in format 304 may be filtered to identify a subset of patient parameters to be parsed and transmitted, such as patient parameters 304D in format 314. As another example, in the illustrated embodiment, configuration interface 214 may forward patient parameter 304D in format 314 to a particular output port and may forward patient parameters 302A and 302C in format 312 to a different output port. As another example, in the illustrated embodiment, configuration interface 214 may forward patient parameters 306A, 306B, 306C in format 306 to a particular output port and forward patient parameter 306C in format 316.

In certain embodiments, configuration interface 214 may include certain configuration parameters, or modifications to configuration parameters, to filter patient parameters and the configuration parameters may be configured by a user. For example, in certain embodiments of the present disclosure, a user may implement configuration interface 214 to specify a selection parameter 322 that indicates the desired patient parameters to be parsed and passed on by configuration interface 214. As another example, in certain embodiments of the present disclosure, a user may implement configuration interface 214 to specify a frequency parameter 320 that indicates the frequency at which the data should be captured and passed (e.g., switching from a 9600 baud rate to a 14400 baud rate).

In certain other embodiments, the frequency parameter 320 may indicate a particular frequency, rate, or time period to receive and transmit (possibly filtered) data. For example, configuration interface 214 may forward patient parameters (or a subset of patient parameters) every second. However, certain receiving systems may not need data every second and, therefore, the frequency parameter 320 may be throttled down to transmit patient parameters (or a subset of patient parameters) every minute, as an example. As another example, the frequency parameter 320 may be throttled up depending on system needs.

As another example, in certain embodiments of the present disclosure, a user may implement configuration interface 214 to specify a compression parameter 324 that indicates certain outputs from a medical device to be captured, compressed, and transmitted together to a receiving system at a specified interval. In certain embodiments, the compression parameter 324 may facilitate capturing data at higher frequencies, and compress desired parameters, discarding others, and transmitting the compressed parameters out at desired intervals, making better use of network bandwidth.

As another example, in certain embodiments of the present disclosure, a user may implement configuration interface 214 to specify an output parameter 326 that indicates a selection of one of several output protocols for transmitting the data to a receiving system. In certain embodiments, the baud rate described above may be specified in the output parameter 326.

As another example, in certain embodiments of the disclosure, a user may implement configuration interface 214 to specify a port parameter 328 that indicates which forwarding port is associated with which output protocol.

According to one exemplary embodiment, configuration interface 214 allows end-users to customize patient parameters and other data that is transmitted from a patient parameter receiving device such as data collection server 104. This may result in a reduction in network traffic and parsing overhead at data collection server 104 and/or application server 106 by selecting a subset of patient parameters and other data to be transmitted.

Figure 4:
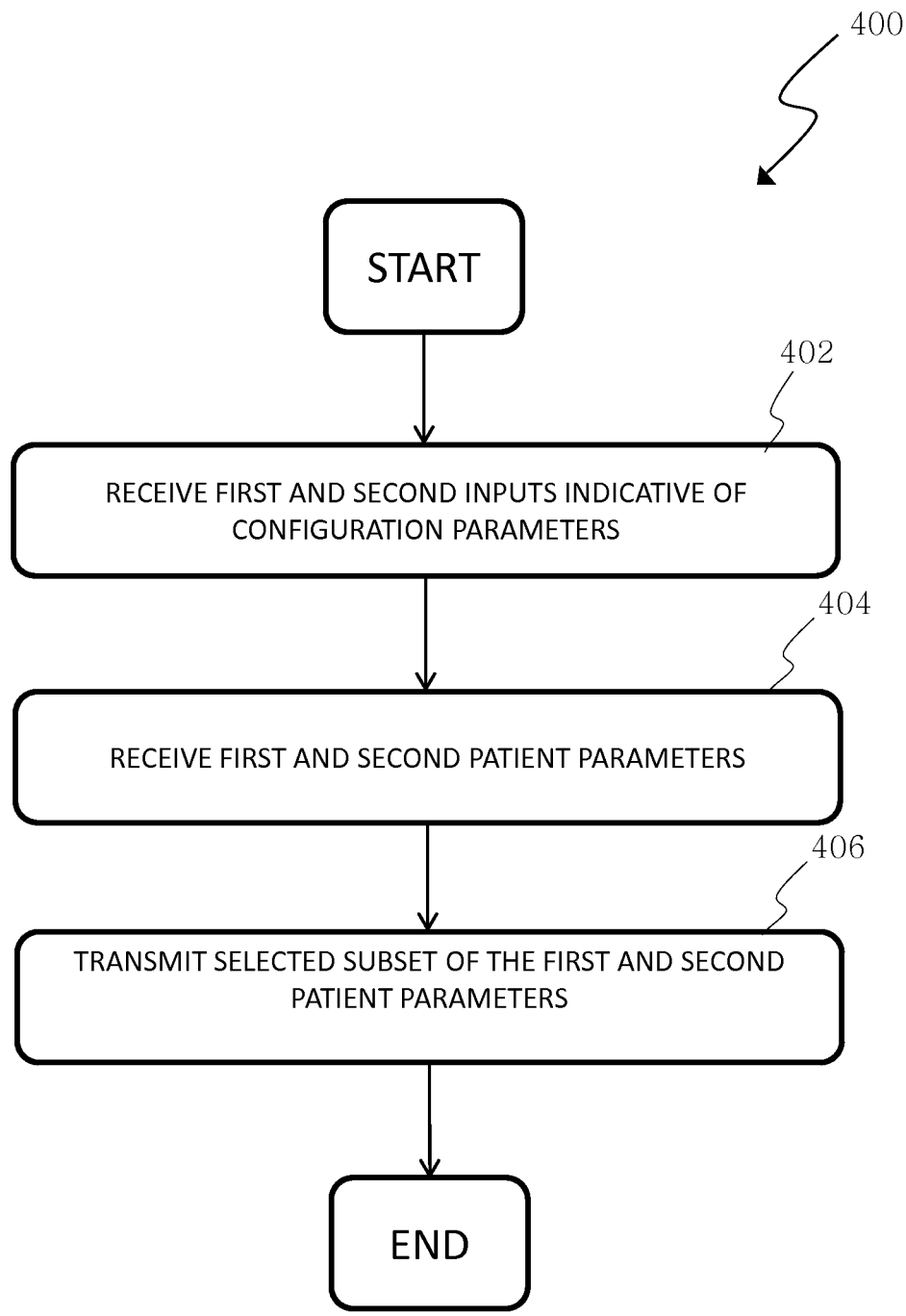
FIG. 4 is a flowchart illustrating a method of receiving and transmitting at least one configuration parameter, in accordance with an aspect of the present disclosure.

FIG. 4 illustrates an example of a method for establishing communication with medical devices, according to certain embodiments of the present disclosure. The method begins at step 402 where a first input indicative of a first configuration parameter for a first medical device from a user and a second input indicative of second configuration parameters for a second medical device from the user are received. The first configuration parameters include at least one of a frequency parameter, a selection parameter, a compression parameter, an output parameter, and a port parameter. At step 404, first patient parameters from the first medical device and second patient parameters from the second medical device are received. At step 406, a first selected subset of the first patient parameters based on the first configuration parameters and a second selected subset of the second patient parameters based on the second configuration parameters are transmitted. It should be understood that some of the steps illustrated in FIG. 4 may be combined, modified or deleted where appropriate, and additional steps may be added to the flowchart. Additionally, as indicated above, steps may be performed in any suitable order without departing from the scope of the present disclosure.

Figure 5:
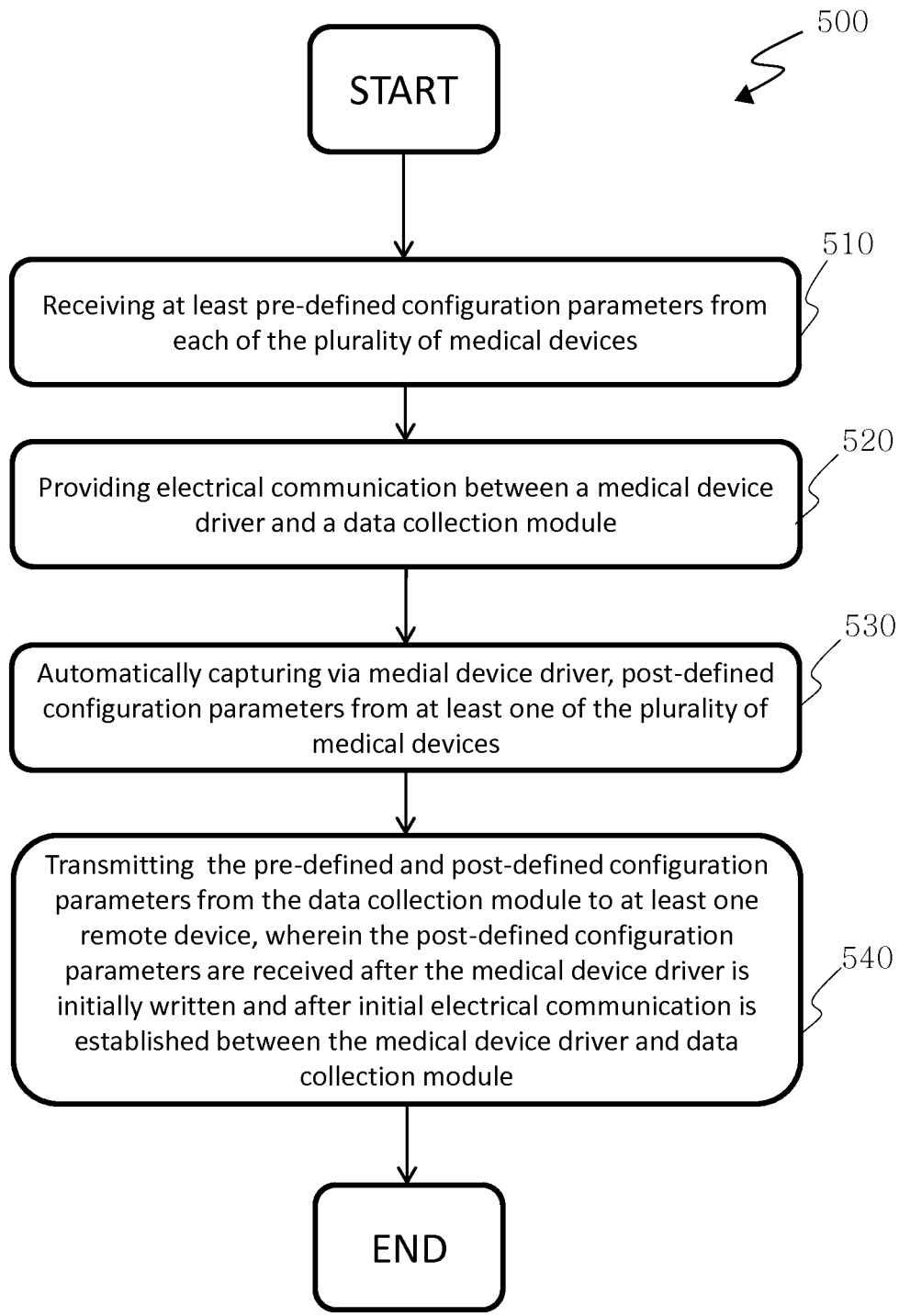
FIG. 5 is a flowchart illustrating a method of establishing communication with a plurality of medical devices, in accordance with an aspect of the present disclosure.

FIG. 5 is a flowchart 500 illustrating a method of establishing communication with a plurality of medical devices, in accordance with an aspect of the present disclosure. In step 510, at least pre-defined configuration parameters are received from each of the plurality of medical devices. In step 520, electrical communication between a medical device driver and a data collection module is provided. In step 530, post-defined configuration parameters from at least one of the plurality of medical devices are automatically captured via the medical device driver. In step 540, the pre-defined and post-defined configuration parameters are transmitted from the data collection module to at least one remote device, wherein the post-defined configuration parameters are received after the medical device driver is initially written and after initial electrical communication is established between the medical device driver and the data collection module. The process then ends. It is to be understood that the method steps described herein need not necessarily be performed in the order as described. Further, words such as "thereafter," "then," "next," etc. are not intended to limit the order of the steps. These words are simply used to guide the reader through the description of the method steps.

Figure 6:
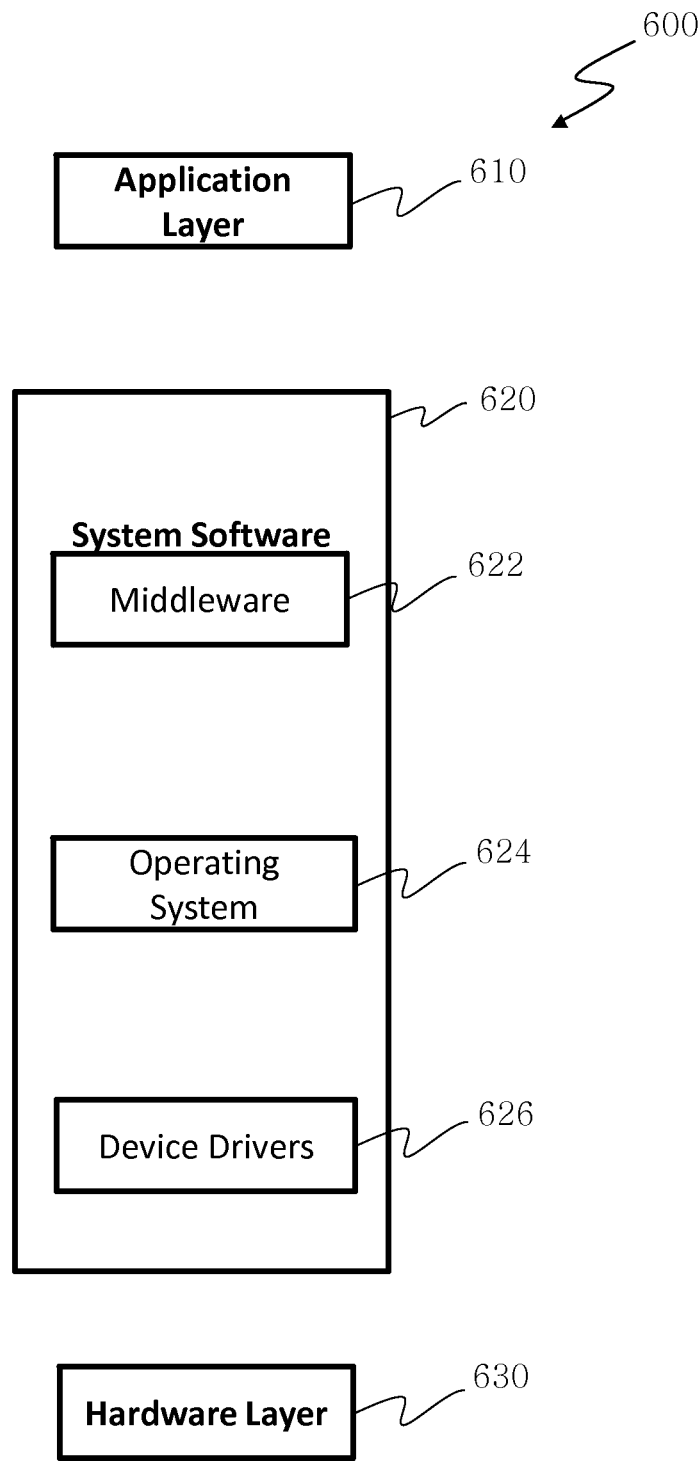
FIG. 6 is an exemplary embedded system architecture illustrating auto-extending device drivers, in accordance with an aspect of the present disclosure.

In FIG. 6, an embedded system architecture illustrating auto-extending device drivers, in accordance with an aspect of the present disclosure is presented. The embedded system 600 includes an application layer 610, a system software layer 620, and a hardware layer 630. The system software layer 620 includes a middleware layer 622, an operating system layer 624, and a device driver layer 626. The device driver layer 626 may be written to allow for auto-extending device driver functionality. The device driver layer 626 will be described in detail with reference to FIGS. 7-10.

Figure 7:
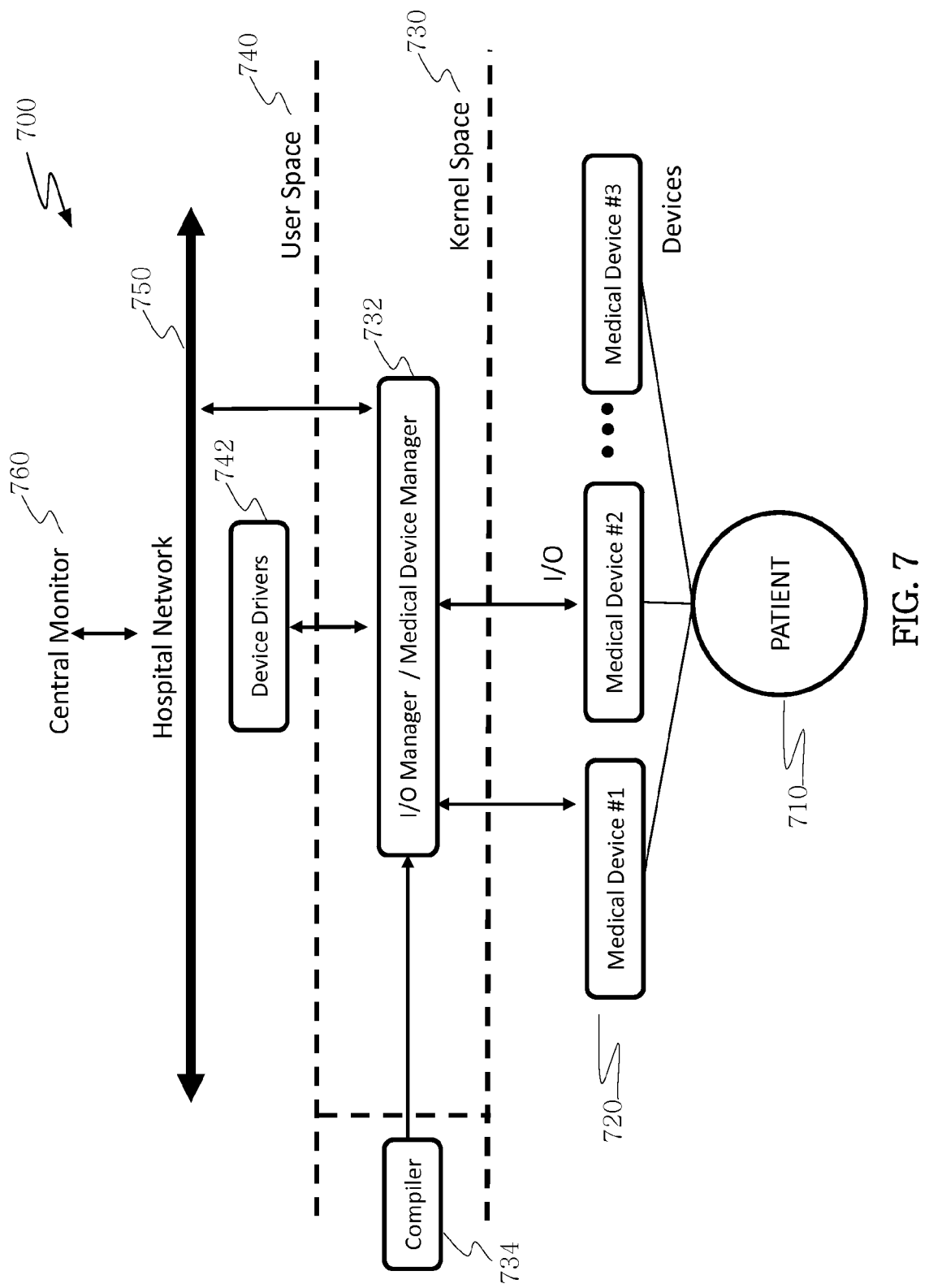
FIG. 7 is a patient monitoring system illustrating auto-extending device drivers, in accordance with an aspect of the present disclosure.

In FIG. 7, a patient monitoring system 700 illustrating auto-extending device drivers, in accordance with an aspect of the present disclosure is presented. The system 700 includes a patient 710 interfacing with a plurality of medical devices 720. The plurality of medical devices 720 may each interface with an I/O Manager or Medical Device Manager 732 located in the kernel space 730. The medical device manager 732 may communicate with a compiler 734. The medical device manager 732 may control the plurality of medical devices 720 via a device driver 742 associated with each of the plurality of medical devices 720. The device drivers may be located in the user space 740. The medical device manager 732 may interface with a hospital network 750 that is connected to a central monitor 760.

Communicating with the medical devices 720 requires the creation of a device driver 742 that may read, parse, and interpret information coming from the output port of the medical devices 720. Medical devices 720 support multiple output protocols for communicating with external systems, such as the hospital network 750 and the central monitor 760. Device drivers 742 are written to capture and parse one or more protocols. The configuration parameters (or physiologic parameters) of each medical device 720 that are captured by the device drivers 742 are not limited to those known at the time that the driver 742 was written. Most medical device manufacturers add more configuration parameters over time to the output protocol that is streamed from the medical devices 720. These newly added configuration parameters may be captured and utilized by the data collection server 104 (see FIG. 1), without upgrading the device driver 742 and/or without rewriting the device driver 742. Thus, a new software patch need not be written each time a new configuration parameter is associated with medical devices 720. Instead, the device driver 742 is an auto-extending device driver 742 that is capable of automatically identifying and capturing newly added or post-defined parameters.

The parameters of the present disclosure have been designated as predefined and post-defined parameters. Predefined parameters refer to parameters that were measured and/or monitored by a medical device at the time the device driver for that medical device was written. Stated differently, the device driver of the medical device was written with the predefined parameters in mind. In contrast, post-defined parameters refer to parameters measured and/or monitored by a medical device after the device driver was written for that medical device. Stated differently, the device driver of the medical device was not written to include the post-defined parameters. The predefined parameters may also be conceptualized as known, familiar, old, initial or native parameters with respect to the device driver. In contrast, post-defined parameters may be conceptualized as unknown or unfamiliar or new or subsequent or non-native parameters with respect to the device driver. Therefore, the parameters described in accordance with the exemplary embodiments of the present disclosure are categorized into parameters known or defined before the device driver was written for the medical device and into parameters unknown or post-defined after the device driver was written for the medical device. The device drives of the exemplary embodiments may also be designated as dynamic drivers, as they have the capability to accommodate post-defined parameters irrespective of when the device drivers were written. Therefore, the device driver need not be re-compiled each time a new parameter is associated with a medical device. The output stream of the medical device is automatically picked up, identified, labeled, and analyzed for the end-user.

Further, in the present disclosure, device drivers 742 send commands to medical devices 720, check medical device status using registers, receive notification of status changes through interrupts, and initiate bulk data transfers using direct memory access (DMA). Medical devices 720 have registers, which are read and written by drivers to get status, send commands, and transfer data. The registers comprise I/O ports (accessed using instructions like inb and outb), memory-mapped I/O, and PCI-configuration registers. Each register is identified by a type and an address. Contiguous sets of registers constitute a range, identified by type, base address, and limit (e.g., the number of addresses in the range). For all register types, access is parameterized by an address, a size, and, for writes, a value of the given size.

Moreover, according to the exemplary embodiments of the present disclosure, an end user, such as a clinician or medical professional, may label the newly added or post-defined parameters as he/she sees fit. For example, the medical professional may specify one or more codes or offsets to be passed to the device driver 742 that may be used to parse for data or information. Regarding the offset, when parsing data from devices, a value may be obtained from a specific offset according to a manufacturer's algorithm description. The medical professional may also specify one or more labels to be associated with the captured data related to the newly added configuration parameters. Further, the medical professional may optionally identify or specify a length of each parameter, a data type of each parameter, and an abbreviation for each parameter. Of course, one skilled in the art may contemplate specifying any type of data or information related to one or more configuration parameters received from one or more medical devices 720. There is no limit to the number of items that may be specified regarding the newly added or post-defined parameters. Therefore, the device drivers 742 are written in such a way as to take into account any configuration parameters that were not previously associated with the medical devices 720, parse for them, and pass them along to the rest of the system as if they were natively supported parameters. Therefore, this system prevents the rewriting of the device drivers 742 of the medical devices 740 each time a new parameter is associated with the medical devices 720.

Figure 8:
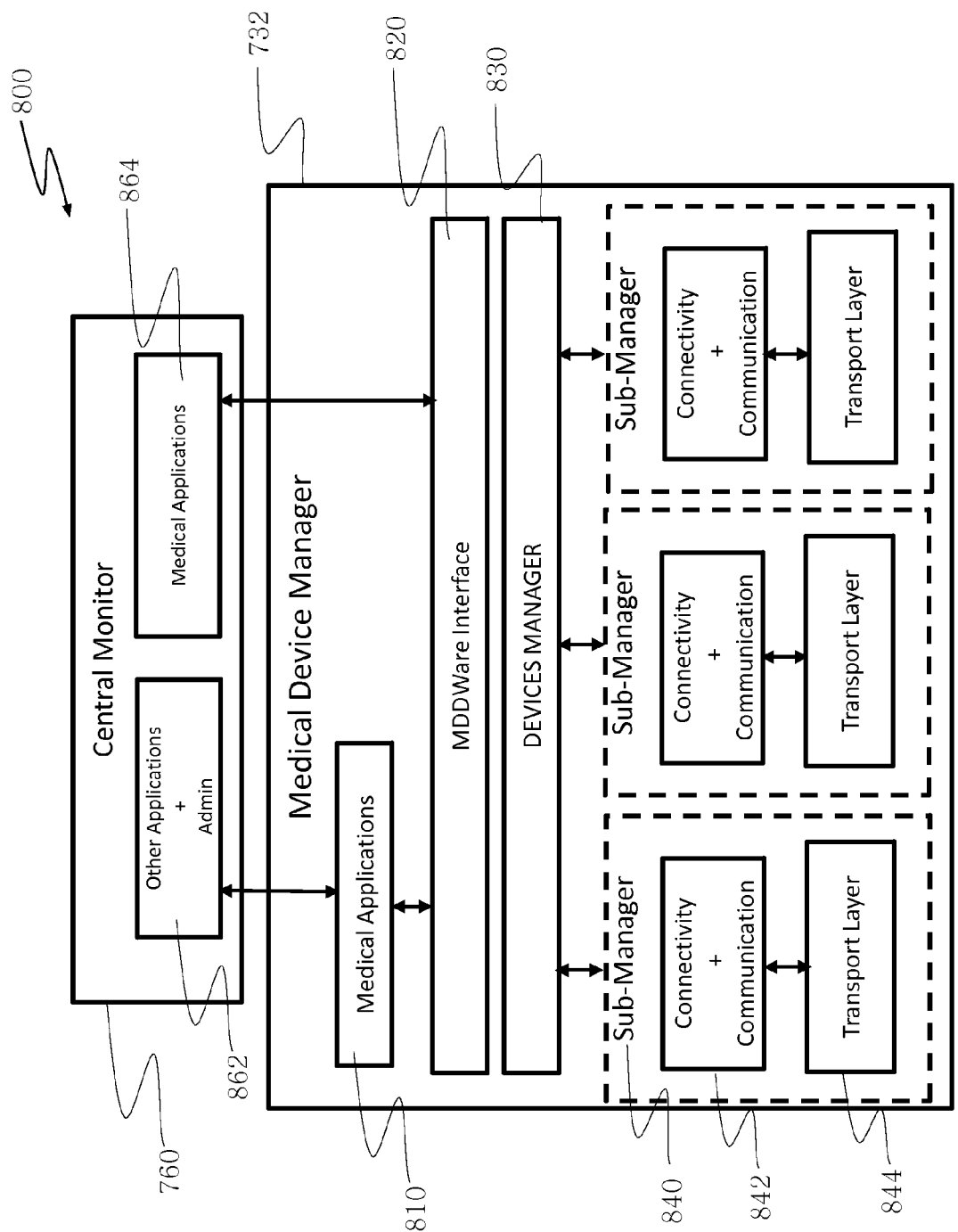
FIG. 8 depicts exemplary interior components of a medical device manager, in accordance with an aspect of the present disclosure.

FIG. 8 shows the medical device manager architecture 800. The medical device manager 732 mainly performs managerial and control tasks. The medical device manager 732 maintains a list of medical devices 720 currently connected to the patient 710 (see FIG. 7). The medical device manager 732 may create sub-managers 840 for each connected medical device 720 and maintains all the sub-managers 840 through the duration of the connection and then destroys sub-manager once the connection is terminated. Thus, each sub-manager 840 is responsible for one medical device of the plurality of medical devices 720. However, one skilled in the art may contemplate one sub-manager being responsible for a plurality of medical devices. Each sub-manager 840 may include a connectivity and communication layer 842 and a transport layer 844. Each sub-manager 840 establishes a connection with a medical device 720 and exchanges packets with the medical device 720 on behalf of medical applications and other modules. The MDDWare Interface 820 sits on top of the MDD Manager 830. The MDDWare Interface 820 is designed to provide a transparent interface for applications that request the services of the MDD Manager 830.

The medical device manager 732 may communicate with a central monitor 760 including administrative applications 862 and medical applications 864. Of course, one skilled in the art may contemplate a plurality of different external devices connected to the medical device manager 732, as well as a plurality of different applications associated with the central monitor 760. Moreover, the medical device manager 732 may include medical applications 810.

Figure 9:
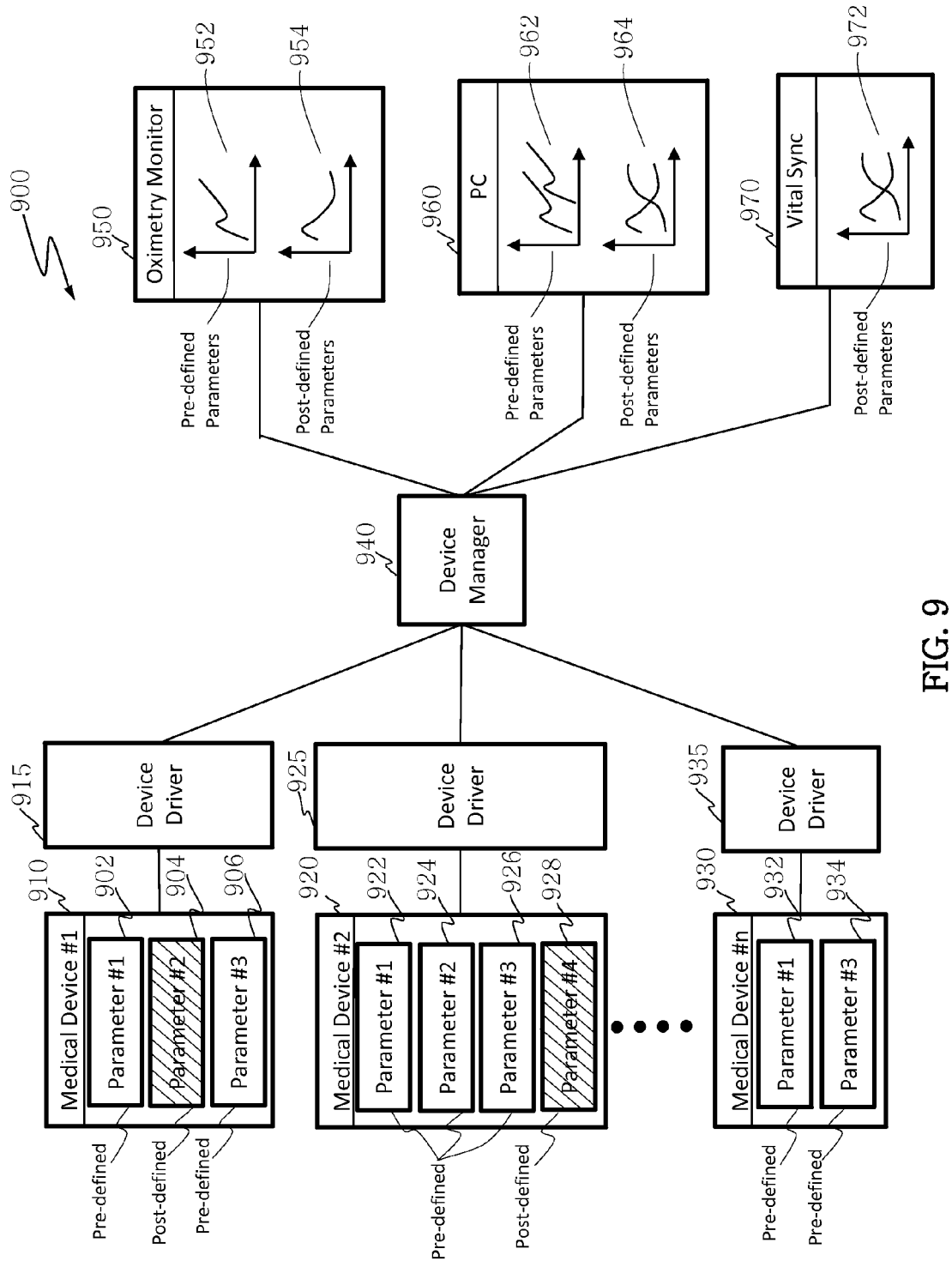
FIG. 9 is a system illustrating the pre-defined and post-defined configuration parameters captured by the device drivers and displayed on a plurality of monitors of external devices, in accordance with an aspect of the present disclosure.

FIG. 9 is a system 900 illustrating the pre-defined and post-defined configuration parameters captured by the device drivers and displayed on a plurality of monitors, in accordance with an aspect of the present disclosure. The system 900 illustrates a plurality of medical devices 910, 920, 930. The first medical device 910 provides, for example, a first parameter 902, a second parameter 904, and a third parameter 906. The first and third parameters 902, 906 may be pre-defined configurations parameters, whereas the second parameter 904 may be a post-defined configuration parameter. The device driver 915 is an auto-extending device driver that captures both the pre-defined and the post-defined configuration parameters.

Similarly, the second medical device 920 provides, for example, a first parameter 922, a second parameter 924, a third parameter 926, and a fourth parameter 928. The first, second, and third parameters 922, 924, 926 may be pre-defined configurations parameters, whereas the fourth parameter 928 may be a post-defined configuration parameter. The device driver 925 is an auto-extending device driver that captures both the pre-defined and the post-defined configuration parameters.

Similarly, the third medical device 930 provides, for example, a first parameter 932 and a second parameter 934. The first and second parameters 932, 934 may be pre-defined configurations parameters. The device driver 935 is an auto-extending device driver that captures both the pre-defined and the post-defined configuration parameters.

The pre-defined and post-defined configuration parameters captured by the device drivers 915, 925, 935 may be transmitted to a device manager 940, as described above in detail with reference to FIG. 8. The device manager 940 may then transmit one or more pre-defined or post-defined parameters to one or more remote devices 950, 960, 970. Device 950 may be an oximetry monitor for displaying a pre-defined parameter 952 and a post-defined parameter 954, as selected by a medical professional. It is contemplated that an end-user may select any pre-defined or post-defined parameters from any of the plurality of medical devices 910, 920, 930. Device 960 may be a PC or laptop or tablet or computing system for displaying a pre-defined parameter 962 and a post-defined parameter 964, as selected by a medical professional. Device 970 may be any type of Vital Sync® system having one or more monitors for displaying a post-defined parameter 972. It is contemplated that the device manager 940 may send the information or data related to the pre-defined or post-defined configuration parameters to any number of external devices or remote devices. Therefore, in accordance with FIG. 9, the post-defined configuration parameters are received after the medical device drivers 915, 925, 935 are initially written and after initial electrical communication has been established between the medical device drivers 915, 925, 935 and the data collection module 104 (see FIG. 1).

It is noted that the remote devices 950, 960, 970 may be cloud devices. The term "cloud" may refer to "cloud computing." Cloud computing may refer at least to at least computation, software, data access, and storage services that do not require end-user knowledge of the physical location and configuration of the system that delivers the services. Cloud computing may also refer to at least a model for enabling convenient, on-demand network access to a shared pool of configurable computing resources (e.g., networks, servers, storage, applications, and services) that may be rapidly provisioned and released with minimal management effort or service provider interaction.

Figure 10:
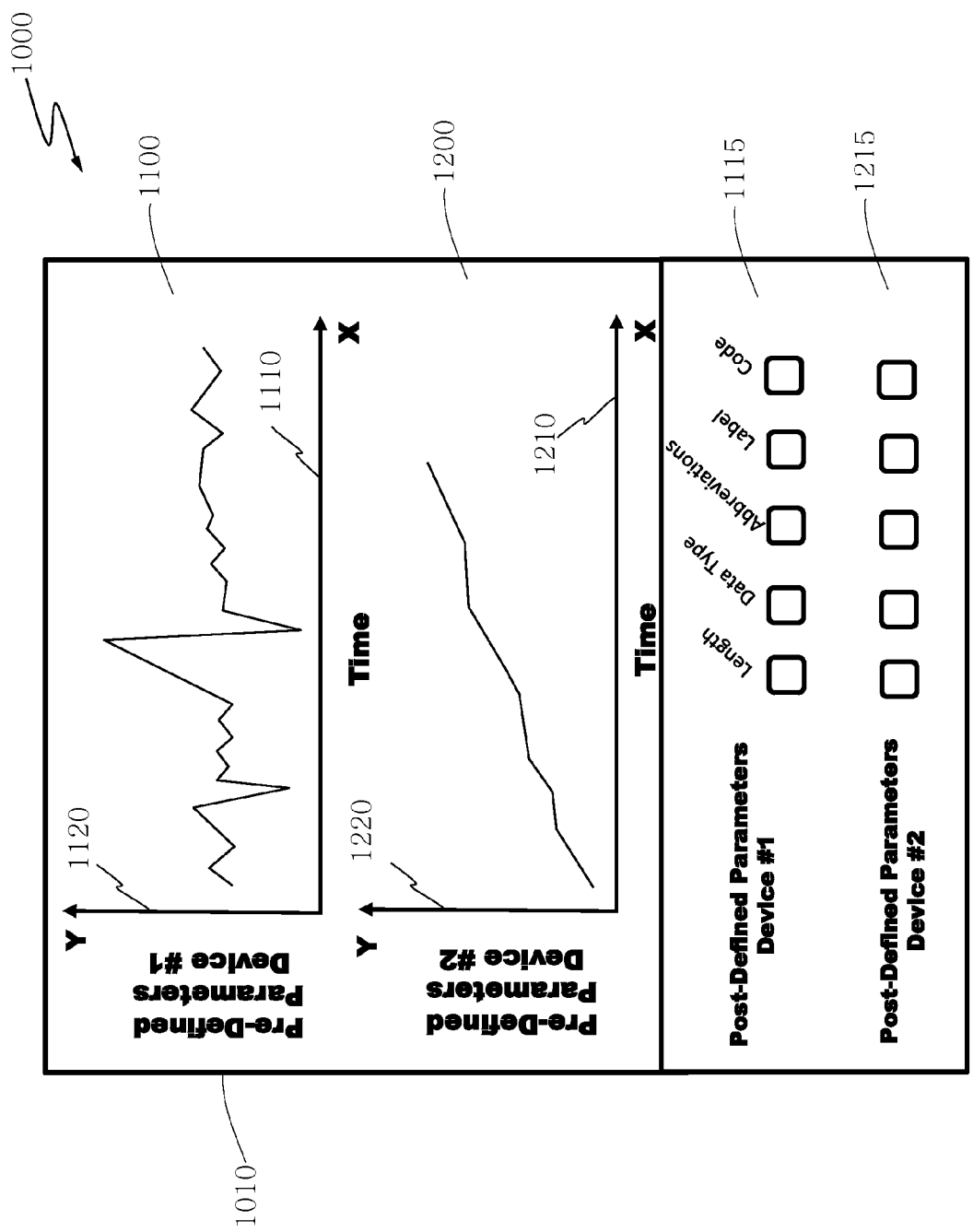
FIG. 10 is an exemplary display for displaying and labeling the post-defined configuration parameters captured by the device drivers, in accordance with an aspect of the present disclosure.

FIG. 10 is a display 1000 for displaying and labeling the post-defined configuration parameters captured by the device drivers, in accordance with an aspect of the present disclosure. The display 1000 includes a monitor 1010 for displaying graphical representations of pre-defined or post-defined configuration parameters selected by a medical professional. For example, graphical representation 1100 depicts a post-defined configuration parameter received from a first medical device and graphical representation 1200 depicts a post-defined configuration parameter received from a second medical device. In plot 1100, the x-axis 1110 represents time, whereas the y-axis 1120 represent the post-defined configuration parameter received from the first medical device. In plot 1200, the x-axis 1210 represents time, whereas the y-axis 1220 represent the post-defined configuration parameter received from the second medical device. Additionally, the monitor 1010 may also display various labels or identifiers related to each of the configuration parameters displayed in a graphical manner. For example, designations 1115 and 1215 may specify indicators such as length of the parameters, data type of the parameters, abbreviation of the parameters, labels and codes or offsets related to the parameters. One skilled in the art may contemplate a plurality of different visual schemes to represent the data or information.

In summary, at least one advantage of the exemplary embodiments of the present disclosure is that it allows for the capture and display of configuration parameters from a plurality of medical devices as soon as those newly added (or post-defined) configuration parameters become available without the need to rewrite the device driver in order to support the newly added (or post-defined) configuration parameters.

Alternatively or additionally, the data/information, indicators, and/or metrics may be displayed in various forms to the user to assist in determining a screen result or monitoring the patient. Although the processes and methods are described below for exemplary purposes with respect to screening patients, the present disclosure is not limited to screening, as it is contemplated that the aspects and features of the present disclosure be applicable for use in the monitoring of physiologic parametric levels for any suitable purpose. Obviously, the settings, parameters, and thresholds may change depending on a particular purpose. However, the general features and aspects of the present disclosure remain generally consistent regardless of the particular purpose. Further, the features and aspects of the present disclosure may be implemented in system 100 in any suitable fashion, e.g., via the hardware and software configuration of system 100 or using any other suitable software, firmware, and/or hardware.

For instance, when implemented via executable instructions, various elements of the present disclosure are in essence the code defining the operations of such various elements. The executable instructions or code may be obtained from a readable medium (e.g., a hard drive media, optical media, EPROM, EEPROM, tape media, cartridge media, flash memory, ROM, memory stick, and/or the like) or communicated via a data signal from a communication medium (e.g., the Internet). In fact, readable media may include any medium that may store or transfer information.

The computer means or computing means or processing means may be operatively associated with the assembly, and is directed by software to compare the first output signal with a first control image and the second output signal with a second control image. The software further directs the computer to produce diagnostic output. Further, a means for transmitting the diagnostic output to an operator of the verification device is included. Thus, many applications of the present disclosure could be formulated. The exemplary network disclosed herein may include any system for exchanging data or transacting business, such as the Internet, an intranet, an extranet, WAN (wide area network), LAN (local area network), satellite communications, and/or the like. It is noted that the network may be implemented as other types of networks.

Additionally, "code" as used herein, or "program" as used herein, may be any plurality of binary values or any executable, interpreted or compiled code which may be used by a computer or execution device to perform a task. This code or program may be written in any one of several known computer languages. A "computer," as used herein, may mean any device which stores, processes, routes, manipulates, or performs like operation on data. A "computer" may be incorporated within one or more transponder recognition and collection systems or servers to operate one or more processors to run the transponder recognition algorithms. Moreover, computer-executable instructions include, for example, instructions and data which cause a general purpose computer, special purpose computer, or special purpose processing device to perform a certain function or group of functions. Computer-executable instructions also include program modules that may be executed by computers in stand-alone or network environments. Generally, program modules include routines, programs, objects, components, and data structures, etc. that perform particular tasks or implement particular abstract data types.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure.

While several embodiments of the disclosure have been shown in the drawings and described in detail hereinabove, it is not intended that the disclosure be limited thereto, as it is intended that the disclosure be as broad in scope as the art will allow. Therefore, the above description and appended drawings should not be construed as limiting, but merely as exemplifications of particular embodiments. Those skilled in the art will envision other modifications within the scope and spirit of the claims appended hereto.

What is claimed is:

1. A medical device communication system, comprising:
a plurality of medical devices;
a data collection module for receiving at least pre-defined configuration parameters from each of the plurality of medical devices;
a medical device driver electrically communicating with the data collection module, the medical device driver automatically capturing post-defined configuration parameters from at least one of the plurality of medical devices; and
at least one remote device configured to receive the pre-defined and post-defined configuration parameters from the data collection module and the medical device driver, respectively;
wherein the post-defined configuration parameters are received from the medical device driver after the medical device driver is initially written and after initial electrical communication is established between the medical device driver and the data collection module.

2. The system according to claim 1, wherein the pre-defined and post-defined configuration parameters are at least one of a frequency parameter, a selection parameter, a compression parameter, an output parameter, and a port parameter.

3. The system according to claim 1, wherein the at least one remote device includes an oximetry monitor configured to display the pre-defined and post-defined configuration parameters.

4. The system according to claim 1, wherein the post-defined configuration parameters are provided with identification information.

5. The system according to claim 4, wherein the identification information includes one or mode codes or offsets to facilitate parsing of the post-defined configuration parameters by the medical device driver.

6. The system according to claim 4, wherein the identification information includes one or more labels associated with the post-defined configuration parameters.

7. The system according to claim 4, wherein the identification information includes at least one of a length, a data type, and an abbreviation of the post-defined configuration parameters.

8. The system according to claim 1, wherein the medical device driver is prevented from being re-written each time post-defined configuration parameters are transmitted from at least one of the plurality of medical devices to the data collection module.

9. A method of establishing communication with a plurality of medical devices, the method comprising:
receiving at least pre-defined configuration parameters from each of the plurality of medical devices;
providing electrical communication between a medical device driver and a data collection module;
automatically capturing, via the medical device driver, post-defined configuration parameters from at least one of the plurality of medical devices; and
transmitting the pre-defined and post-defined configuration parameters from the data collection module and the medical device driver, respectively, to at least one remote device;
wherein the post-defined configuration parameters are received from the medical device driver after the medical device driver is initially written and after initial electrical communication is established between the medical device driver and the data collection module.

10. The method according to claim 9, wherein the pre-defined and post-defined configuration parameters are at least one of a frequency parameter, a selection parameter, a compression parameter, an output parameter, and a port parameter.

11. The method according to claim 9, further comprising providing the post-defined configuration parameters with identification information.

12. The method according to claim 11, wherein the identification information includes one or mode codes or offsets to facilitate parsing of the post-defined configuration parameters by the medical device driver.

13. The method according to claim 11, wherein the identification information includes one or more labels associated with the post-defined configuration parameters.

14. The method according to claim 11, wherein the identification information includes at least one of a length, a data type, and an abbreviation of the post-defined configuration parameters.

15. The method according to claim 9, further comprising preventing the medical device driver from being re-written each time post-defined configuration parameters are transmitted from at least one of the plurality of medical devices to the data collection module.

16. A non-transitory computer-readable storage medium encoded with a program that, when executed by a processor, causes the processor to:
   receive at least pre-defined configuration parameters from each of the plurality of medical devices;
   provide electrical communication between a medical device driver and a data collection module;
   automatically capture, via the medical device driver, post-defined configuration parameters from at least one of the plurality of medical devices; and
   transmit the pre-defined and post-defined configuration parameters from the data collection module and the medical device driver, respectively, to at least one remote device;
   wherein the post-defined configuration parameters are received from the medical device driver after the medical device driver is initially written and after initial electrical communication is established between the medical device driver and the data collection module.

17. The non-transitory computer-readable storage medium of claim 16, wherein the processor is further caused to provide the post-defined configuration parameters with identification information.

18. The non-transitory computer-readable storage medium of claim 17,
   wherein the identification information includes one or mode codes or offsets to facilitate parsing of the post-defined configuration parameters by the medical device driver; and
   wherein identification information includes one or more labels associated with the post-defined configuration parameters.

19. The non-transitory computer-readable storage medium of claim 17, wherein the identification information includes at least one of a length, a data type, and an abbreviation of the post-defined configuration parameters.

20. The non-transitory computer-readable storage medium of claim 16, wherein the processor is further caused to prevent the medical device driver from being re-written each time post-defined configuration parameters are transmitted from at least one of the plurality of medical devices to the data collection module.

* * * * *